US008834486B2

(12) United States Patent
Metzger et al.

(10) Patent No.: US 8,834,486 B2
(45) Date of Patent: *Sep. 16, 2014

(54) FEMORAL GUIDE FOR IMPLANTING A FEMORAL KNEE PROSTHESIS

(75) Inventors: Robert Metzger, Wakarusa, IN (US); Jacy C. Hoeppner, Warsaw, IN (US)

(73) Assignee: Biomet Manufacturing, LLC, Warsaw, IN (US)

(*) Notice: Subject to any disclaimer, the term of this patent is extended or adjusted under 35 U.S.C. 154(b) by 259 days.

This patent is subject to a terminal disclaimer.

(21) Appl. No.: 13/401,354

(22) Filed: Feb. 21, 2012

(65) Prior Publication Data

US 2012/0150189 A1   Jun. 14, 2012

Related U.S. Application Data

(63) Continuation of application No. 12/367,903, filed on Feb. 9, 2009, now Pat. No. 8,123,758, which is a continuation of application No. 10/730,456, filed on Dec. 8, 2003, now Pat. No. 7,488,324.

(51) Int. Cl.
*A61B 17/58* (2006.01)
*A61B 17/15* (2006.01)

(52) U.S. Cl.
CPC .................. *A61B 17/155* (2013.01)
USPC .......................................... 606/102

(58) Field of Classification Search
USPC ................. 606/86–89, 96, 102, 86 R–89
See application file for complete search history.

(56) References Cited

U.S. PATENT DOCUMENTS

| | | | |
|---|---|---|---|
| 1,763,730 | A | 6/1930 | Von Lackum |
| 1,920,821 | A | 8/1933 | Jacob |
| 1,959,615 | A | 5/1934 | Derrah |
| 2,433,815 | A | 12/1947 | LaForge |
| 2,455,655 | A | 12/1948 | Carroll |
| 2,702,550 | A | 2/1955 | Rowe |
| 2,724,326 | A | 11/1955 | Long |

(Continued)

FOREIGN PATENT DOCUMENTS

| | | |
|---|---|---|
| CH | 117960 | 5/1927 |
| DE | 337437 | 5/1921 |

(Continued)

OTHER PUBLICATIONS

"AGC 3000 Intramedullary Surgical Technique Using PMMA Fixation," 1987, Biomet, Inc.

(Continued)

*Primary Examiner* — Howie Matthews
(74) *Attorney, Agent, or Firm* — Harness, Dickey (57) ABSTRACT

Disclosed is a method of selecting a femoral prosthetic for implantation relative to a femur using a femoral sizing guide. An extension portion of the femoral sizing guide is placed adjacent to a posterior condyle surface of the femur. A stylus is located proximate to an interior condyle surface of the femur. A first actuator disposed between the extension portion and a base portion is moved to rotatably displace the extension portion with respect to the base portion until the stylus is centrally located on top of the interior condyle. A measurement of the femur is identified with the sizing guide based on a relative location of the stylus, the extension portion and the base portion. A femoral prosthesis is selected based on the measurement.

18 Claims, 9 Drawing Sheets

(56) References Cited

U.S. PATENT DOCUMENTS

| | | |
|---|---|---|
| 2,951,482 A | 9/1960 | Sullivan |
| 2,955,530 A | 10/1960 | Nilo |
| 3,048,522 A | 8/1962 | Velley |
| 3,229,006 A | 1/1966 | Nohl |
| 3,514,791 A | 6/1970 | Sparks |
| 3,554,197 A | 1/1971 | Dobbie |
| 3,624,747 A | 11/1971 | McKnight et al. |
| 3,631,596 A | 1/1972 | Glaus |
| 3,678,934 A | 7/1972 | Warfield et al. |
| 3,698,017 A | 10/1972 | Scales et al. |
| 3,703,036 A | 11/1972 | Karubian |
| 3,774,244 A | 11/1973 | Walker |
| 3,783,873 A | 1/1974 | Jacobs |
| 3,807,393 A | 4/1974 | McDonald |
| 3,811,449 A | 5/1974 | Gravlee et al. |
| 3,869,731 A | 3/1975 | Waugh et al. |
| 3,903,549 A | 9/1975 | Deyerle |
| 3,905,105 A | 9/1975 | Tuke |
| 3,905,374 A | 9/1975 | Winter |
| 3,911,923 A | 10/1975 | Yoon |
| 3,913,585 A | 10/1975 | Wolvek |
| 3,920,022 A | 11/1975 | Pastor |
| 3,941,127 A | 3/1976 | Froning |
| 3,967,625 A | 7/1976 | Yoon |
| 3,989,049 A | 11/1976 | Yoon |
| 3,991,426 A | 11/1976 | Flom et al. |
| 3,994,287 A | 11/1976 | Turp et al. |
| 4,053,953 A | 10/1977 | Flom et al. |
| 4,055,862 A | 11/1977 | Farling |
| 4,081,866 A | 4/1978 | Upshaw et al. |
| 4,085,466 A | 4/1978 | Goodfellow et al. |
| 4,085,743 A | 4/1978 | Yoon |
| 4,103,680 A | 8/1978 | Yoon |
| 4,299,224 A | 11/1981 | Noiles |
| 4,304,178 A | 12/1981 | Haberle |
| 4,311,145 A | 1/1982 | Esty et al. |
| 4,344,193 A | 8/1982 | Kenny |
| 4,349,018 A | 9/1982 | Chambers |
| 4,373,709 A | 2/1983 | Whitt |
| 4,374,523 A | 2/1983 | Yoon |
| 4,385,404 A | 5/1983 | Sully et al. |
| 4,386,609 A | 6/1983 | Mongeon |
| 4,400,833 A | 8/1983 | Kurland |
| D273,895 S | 5/1984 | Kenna |
| D274,091 S | 5/1984 | Kenna |
| 4,453,421 A | 6/1984 | Umano |
| 4,501,269 A | 2/1985 | Bagby |
| 4,509,518 A | 4/1985 | McGarry et al. |
| 4,516,276 A | 5/1985 | Mittelmeier et al. |
| 4,534,365 A | 8/1985 | Bonetta et al. |
| 4,545,375 A | 10/1985 | Cline |
| 4,554,686 A | 11/1985 | Baker |
| 4,562,598 A | 1/1986 | Kranz |
| 4,565,192 A | 1/1986 | Shapiro |
| 4,567,886 A | 2/1986 | Petersen |
| 4,574,794 A | 3/1986 | Cooke et al. |
| 4,619,391 A | 10/1986 | Sharkany et al. |
| 4,624,254 A | 11/1986 | McGarry et al. |
| 4,641,648 A | 2/1987 | Shapiro |
| 4,642,120 A | 2/1987 | Nevo et al. |
| 4,646,729 A | 3/1987 | Kenna et al. |
| 4,662,372 A | 5/1987 | Sharkany et al. |
| 4,678,470 A | 7/1987 | Nashef et al. |
| 4,682,598 A | 7/1987 | Beraha |
| 4,685,460 A | 8/1987 | Thornton |
| 4,703,751 A | 11/1987 | Pohl |
| 4,711,233 A | 12/1987 | Brown |
| 4,718,413 A | 1/1988 | Johnson |
| 4,718,916 A | 1/1988 | Morscher |
| 4,739,751 A | 4/1988 | Sapega et al. |
| 4,794,854 A | 1/1989 | Swaim |
| 4,817,602 A | 4/1989 | Beraha |
| 4,834,757 A | 5/1989 | Brantigan |
| 4,838,891 A | 6/1989 | Branemark et al. |
| 4,863,472 A | 9/1989 | Tormala et al. |
| 4,888,022 A | 12/1989 | Huebsch |
| 4,911,721 A | 3/1990 | Bränemark et al. |
| 4,935,023 A | 6/1990 | Whiteside et al. |
| 4,936,852 A | 6/1990 | Kent et al. |
| 4,950,296 A | 8/1990 | McIntyre |
| 4,952,213 A | 8/1990 | Bowman et al. |
| 4,961,740 A | 10/1990 | Ray et al. |
| 4,961,954 A | 10/1990 | Goldberg et al. |
| 4,964,865 A | 10/1990 | Burkhead et al. |
| 4,979,949 A | 12/1990 | Matsen, III et al. |
| 4,979,957 A | 12/1990 | Hodorek |
| 4,985,031 A | 1/1991 | Buss et al. |
| 4,985,038 A | 1/1991 | Lyell |
| 5,007,912 A | 4/1991 | Albrektsson et al. |
| 5,015,247 A | 5/1991 | Michelson |
| 5,032,132 A | 7/1991 | Matsen, III et al. |
| 5,035,700 A | 7/1991 | Kenna |
| 5,060,678 A | 10/1991 | Bauman et al. |
| 5,061,286 A | 10/1991 | Lyle |
| 5,062,843 A | 11/1991 | Mahony, III |
| 5,073,373 A | 12/1991 | O'Leary et al. |
| 5,082,670 A | 1/1992 | Gage et al. |
| 5,084,050 A | 1/1992 | Draenert |
| 5,092,869 A | 3/1992 | Waldron |
| 5,098,436 A | 3/1992 | Ferrante et al. |
| 5,098,437 A | 3/1992 | Kashuba et al. |
| 5,099,859 A | 3/1992 | Bell |
| 5,100,689 A | 3/1992 | Goldberg et al. |
| 5,101,720 A | 4/1992 | Bianchi |
| 5,108,441 A | 4/1992 | McDowell |
| 5,111,987 A | 5/1992 | Moeinzadeh et al. |
| 5,122,144 A | 6/1992 | Bert et al. |
| 5,123,906 A | 6/1992 | Kelman |
| 5,129,909 A | 7/1992 | Sutherland |
| 5,147,365 A | 9/1992 | Whitlock et al. |
| 5,152,744 A | 10/1992 | Krause et al. |
| 5,152,778 A | 10/1992 | Bales, Jr. et al. |
| 5,154,717 A | 10/1992 | Matsen, III et al. |
| 5,162,506 A | 11/1992 | Hadden |
| 5,163,949 A | 11/1992 | Bonutti |
| 5,170,800 A | 12/1992 | Smith et al. |
| 5,171,243 A | 12/1992 | Kashuba et al. |
| 5,171,244 A | 12/1992 | Caspari et al. |
| 5,171,276 A | 12/1992 | Caspari et al. |
| 5,174,300 A | 12/1992 | Bales et al. |
| 5,176,702 A | 1/1993 | Bales et al. |
| 5,178,622 A | 1/1993 | Lehner, II |
| 5,183,053 A | 2/1993 | Yeh et al. |
| 5,183,464 A | 2/1993 | Dubrul et al. |
| 5,186,178 A | 2/1993 | Yeh et al. |
| 5,192,327 A | 3/1993 | Brantigan |
| 5,197,968 A | 3/1993 | Clement |
| 5,197,971 A | 3/1993 | Bonutti |
| 5,197,987 A | 3/1993 | Koch et al. |
| 5,204,106 A | 4/1993 | Schepers et al. |
| 5,207,680 A | 5/1993 | Dietz et al. |
| 5,207,692 A | 5/1993 | Kraus et al. |
| 5,217,463 A | 6/1993 | Mikhail |
| 5,228,459 A | 7/1993 | Caspari et al. |
| 5,234,433 A | 8/1993 | Bert et al. |
| 5,242,448 A | 9/1993 | Pettine et al. |
| 5,258,004 A | 11/1993 | Bales et al. |
| 5,263,498 A | 11/1993 | Caspari et al. |
| 5,263,987 A | 11/1993 | Shah |
| 5,269,785 A | 12/1993 | Bonutti |
| 5,273,524 A | 12/1993 | Fox et al. |
| D343,247 S | 1/1994 | Walen |
| 5,275,166 A | 1/1994 | Vaitekunas et al. |
| 5,275,603 A | 1/1994 | Ferrante et al. |
| 5,282,803 A | 2/1994 | Lackey |
| 5,285,773 A | 2/1994 | Bonutti et al. |
| 5,293,878 A | 3/1994 | Bales et al. |
| 5,295,994 A | 3/1994 | Bonutti |
| 5,304,181 A | 4/1994 | Caspari et al. |
| 5,306,285 A | 4/1994 | Miller et al. |
| 5,308,349 A | 5/1994 | Mikhail |
| 5,314,482 A | 5/1994 | Goodfellow et al. |
| 5,322,505 A | 6/1994 | Krause et al. |
| 5,329,845 A | 7/1994 | Bichel |

(56) References Cited

U.S. PATENT DOCUMENTS

| | | |
|---|---|---|
| 5,330,468 A | 7/1994 | Burkhart |
| 5,342,367 A | 8/1994 | Ferrante et al. |
| 5,342,368 A | 8/1994 | Petersen |
| 5,344,423 A | 9/1994 | Dietz et al. |
| 5,344,458 A | 9/1994 | Bonutti |
| 5,348,541 A | 9/1994 | Lyell |
| 5,364,401 A | 11/1994 | Ferrante et al. |
| 5,364,402 A | 11/1994 | Mumme et al. |
| 5,368,599 A | 11/1994 | Hirsch et al. |
| 5,379,133 A | 1/1995 | Kirk |
| 5,382,249 A | 1/1995 | Fletcher |
| 5,383,937 A | 1/1995 | Mikhail |
| 5,390,683 A | 2/1995 | Pisharodi |
| 5,395,376 A | 3/1995 | Caspari et al. |
| D358,647 S | 5/1995 | Cohen et al. |
| 5,417,694 A | 5/1995 | Marik et al. |
| 5,423,827 A | 6/1995 | Mumme et al. |
| 5,425,355 A | 6/1995 | Kulick |
| 5,425,745 A | 6/1995 | Green et al. |
| 5,443,475 A | 8/1995 | Auerbach et al. |
| 5,445,639 A | 8/1995 | Kuslich et al. |
| 5,445,642 A | 8/1995 | McNulty et al. |
| 5,454,365 A | 10/1995 | Bonutti |
| 5,454,815 A | 10/1995 | Geisser et al. |
| 5,454,816 A | 10/1995 | Ashby |
| 5,456,268 A | 10/1995 | Bonutti |
| 5,464,407 A | 11/1995 | McGuire |
| 5,472,415 A | 12/1995 | King et al. |
| 5,484,095 A | 1/1996 | Green et al. |
| 5,486,178 A | 1/1996 | Hodge |
| 5,490,854 A | 2/1996 | Fisher et al. |
| 5,497,933 A | 3/1996 | DeFonzo et al. |
| 5,507,763 A | 4/1996 | Petersen et al. |
| 5,514,139 A | 5/1996 | Goldstein et al. |
| 5,514,143 A | 5/1996 | Bonutti et al. |
| 5,520,692 A | 5/1996 | Ferrante |
| 5,520,694 A | 5/1996 | Dance et al. |
| 5,522,897 A | 6/1996 | King et al. |
| 5,540,695 A | 7/1996 | Levy |
| 5,540,696 A | 7/1996 | Booth, Jr. et al. |
| 5,545,222 A | 8/1996 | Bonutti |
| 5,546,720 A | 8/1996 | LaBruzza |
| 5,549,683 A | 8/1996 | Bonutti |
| 5,554,169 A | 9/1996 | Green et al. |
| 5,562,675 A | 10/1996 | McNulty et al. |
| 5,569,163 A | 10/1996 | Francis et al. |
| 5,569,260 A | 10/1996 | Petersen |
| 5,569,261 A | 10/1996 | Marik et al. |
| 5,570,700 A | 11/1996 | Vogeler |
| 5,578,039 A | 11/1996 | Vendrely et al. |
| 5,593,448 A | 1/1997 | Dong |
| 5,597,379 A | 1/1997 | Haines et al. |
| 5,608,052 A | 3/1997 | Zmitek et al. |
| 5,609,603 A | 3/1997 | Linden |
| 5,611,802 A | 3/1997 | Samuelson et al. |
| 5,624,444 A | 4/1997 | Wixon et al. |
| 5,624,463 A | 4/1997 | Stone et al. |
| 5,632,745 A | 5/1997 | Schwartz |
| 5,643,272 A | 7/1997 | Haines et al. |
| 5,649,946 A | 7/1997 | Bramlet |
| 5,649,947 A | 7/1997 | Auerbach et al. |
| 5,653,714 A | 8/1997 | Dietz et al. |
| 5,659,947 A | 8/1997 | Eilers et al. |
| 5,662,656 A | 9/1997 | White |
| 5,662,710 A | 9/1997 | Bonutti |
| 5,667,069 A | 9/1997 | Williams, Jr. |
| 5,667,511 A | 9/1997 | Vendrely et al. |
| 5,667,512 A | 9/1997 | Johnson |
| 5,667,520 A | 9/1997 | Bonutti |
| D385,163 S | 10/1997 | Hutchins et al. |
| 5,681,316 A | 10/1997 | DeOrio et al. |
| 5,683,397 A | 11/1997 | Vendrely et al. |
| 5,683,398 A | 11/1997 | Carls et al. |
| 5,688,279 A | 11/1997 | McNulty et al. |
| 5,688,280 A | 11/1997 | Booth, Jr. et al. |
| 5,694,693 A | 12/1997 | Hutchins et al. |
| 5,702,447 A | 12/1997 | Walch et al. |
| 5,702,475 A | 12/1997 | Zahedi |
| 5,704,941 A | 1/1998 | Jacober et al. |
| 5,707,350 A | 1/1998 | Krause et al. |
| 5,712,543 A | 1/1998 | Sjostrom |
| 5,716,360 A | 2/1998 | Baldwin et al. |
| 5,718,708 A | 2/1998 | Webb |
| 5,720,752 A | 2/1998 | Elliott et al. |
| 5,723,331 A | 3/1998 | Tubo et al. |
| 5,733,292 A | 3/1998 | Gustilo et al. |
| 5,749,876 A | 5/1998 | Duvillier et al. |
| 5,755,731 A | 5/1998 | Grinberg |
| 5,755,791 A | 5/1998 | Whitson et al. |
| 5,755,803 A | 5/1998 | Haines et al. |
| 5,769,855 A | 6/1998 | Bertin et al. |
| 5,769,899 A | 6/1998 | Schwartz et al. |
| 5,772,594 A | 6/1998 | Barrick |
| 5,776,137 A | 7/1998 | Katz |
| 5,788,700 A | 8/1998 | Morawa et al. |
| 5,810,827 A | 9/1998 | Haines et al. |
| 5,810,831 A | 9/1998 | D'Antonio |
| 5,817,097 A | 10/1998 | Howard et al. |
| 5,817,109 A | 10/1998 | McGarry et al. |
| 5,842,477 A | 12/1998 | Naughton et al. |
| 5,846,931 A | 12/1998 | Hattersley et al. |
| 5,860,980 A | 1/1999 | Axelson, Jr. et al. |
| 5,860,981 A | 1/1999 | Bertin et al. |
| 5,866,415 A | 2/1999 | Villeneuve |
| 5,871,493 A | 2/1999 | Sjostrom et al. |
| 5,879,354 A | 3/1999 | Haines et al. |
| 5,888,219 A | 3/1999 | Bonutti |
| 5,899,914 A | 5/1999 | Zirps et al. |
| 5,908,424 A | 6/1999 | Bertin et al. |
| 5,911,723 A | 6/1999 | Ashby et al. |
| 5,913,874 A | 6/1999 | Berns et al. |
| 5,916,219 A | 6/1999 | Matsuno et al. |
| 5,916,220 A | 6/1999 | Masini |
| 5,921,990 A | 7/1999 | Webb |
| 5,925,049 A | 7/1999 | Gustilo et al. |
| 5,961,499 A | 10/1999 | Bonutti et al. |
| 5,997,566 A | 12/1999 | Tobin |
| 6,007,537 A | 12/1999 | Burkinshaw et al. |
| 6,012,456 A | 1/2000 | Schuerch |
| 6,013,081 A | 1/2000 | Burkinshaw et al. |
| 6,015,419 A | 1/2000 | Strome et al. |
| 6,019,767 A | 2/2000 | Howell |
| 6,022,350 A | 2/2000 | Ganem |
| 6,024,746 A | 2/2000 | Katz |
| 6,056,754 A | 5/2000 | Haines et al. |
| 6,056,756 A | 5/2000 | Eng et al. |
| 6,059,788 A | 5/2000 | Katz |
| 6,059,817 A | 5/2000 | Bonutti et al. |
| 6,059,831 A | 5/2000 | Braslow et al. |
| 6,063,095 A | 5/2000 | Wang et al. |
| 6,077,270 A | 6/2000 | Katz |
| 6,077,287 A | 6/2000 | Taylor et al. |
| 6,086,593 A | 7/2000 | Bonutti |
| 6,090,122 A | 7/2000 | Sjostrom et al. |
| 6,096,043 A | 8/2000 | Techiera et al. |
| 6,099,531 A | 8/2000 | Bonutti |
| 6,099,532 A | 8/2000 | Florea |
| 6,102,850 A | 8/2000 | Wang et al. |
| 6,106,529 A | 8/2000 | Techiera |
| 6,118,845 A | 9/2000 | Simon et al. |
| 6,120,509 A | 9/2000 | Wheeler |
| 6,132,472 A | 10/2000 | Bonutti |
| 6,156,070 A | 12/2000 | Incavo et al. |
| 6,159,246 A | 12/2000 | Mendes et al. |
| 6,171,340 B1 | 1/2001 | McDowell |
| 6,174,321 B1 | 1/2001 | Webb |
| 6,185,315 B1 | 2/2001 | Schmucker et al. |
| 6,187,023 B1 | 2/2001 | Bonutti |
| 6,195,158 B1 | 2/2001 | Cadell et al. |
| 6,197,064 B1 | 3/2001 | Haines et al. |
| 6,198,794 B1 | 3/2001 | Peshkin et al. |
| 6,211,976 B1 | 4/2001 | Popovich et al. |
| 6,214,051 B1 | 4/2001 | Badorf et al. |
| 6,228,121 B1 | 5/2001 | Khalili |

(56) References Cited

U.S. PATENT DOCUMENTS

| | | |
|---|---|---|
| 6,258,127 B1 | 7/2001 | Schmotzer |
| 6,277,136 B1 | 8/2001 | Bonutti |
| 6,290,703 B1 | 9/2001 | Ganem |
| 6,290,704 B1 | 9/2001 | Burkinshaw et al. |
| 6,325,806 B1 | 12/2001 | Fox |
| 6,328,572 B1 | 12/2001 | Higashida et al. |
| 6,338,737 B1 | 1/2002 | Toledano |
| 6,344,043 B1 | 2/2002 | Pappas |
| 6,358,266 B1 | 3/2002 | Bonutti |
| 6,361,565 B1 | 3/2002 | Bonutti |
| 6,391,040 B1 | 5/2002 | Christoudias |
| 6,406,495 B1 | 6/2002 | Schoch |
| 6,409,722 B1 | 6/2002 | Hoey et al. |
| 6,423,063 B1 | 7/2002 | Bonutti |
| 6,431,743 B1 | 8/2002 | Mizutani et al. |
| D462,767 S | 9/2002 | Meyer et al. |
| 6,458,135 B1 | 10/2002 | Harwin et al. |
| 6,468,280 B1 | 10/2002 | Saenger et al. |
| 6,468,289 B1 | 10/2002 | Bonutti |
| 6,478,799 B1 | 11/2002 | Williamson |
| 6,482,209 B1 | 11/2002 | Engh et al. |
| 6,500,179 B1 | 12/2002 | Masini |
| 6,500,181 B1 | 12/2002 | Portney |
| 6,503,267 B2 | 1/2003 | Bonutti et al. |
| 6,554,837 B1 | 4/2003 | Hauri et al. |
| 6,554,838 B2 | 4/2003 | McGovern et al. |
| 6,558,391 B2 | 5/2003 | Axelson, Jr. et al. |
| 6,571,132 B1 | 5/2003 | Davis et al. |
| 6,575,982 B1 | 6/2003 | Bonutti |
| 6,602,259 B1 | 8/2003 | Masini |
| 6,620,181 B1 | 9/2003 | Bonutti |
| 6,632,225 B2 | 10/2003 | Sanford et al. |
| 6,635,073 B2 | 10/2003 | Bonutti |
| 6,673,077 B1 | 1/2004 | Katz |
| 6,676,662 B1 | 1/2004 | Bagga et al. |
| 6,695,848 B2 | 2/2004 | Haines |
| 6,702,821 B2 | 3/2004 | Bonutti |
| 6,770,078 B2 | 8/2004 | Bonutti |
| 6,916,325 B2 | 7/2005 | Kana et al. |
| 6,979,299 B2 | 12/2005 | Peabody et al. |
| 7,029,477 B2 | 4/2006 | Grimm |
| 7,172,599 B2 | 2/2007 | Steffensmeier et al. |
| 7,261,719 B1 | 8/2007 | Twomey et al. |
| 7,344,541 B2 | 3/2008 | Haines et al. |
| 7,488,324 B1 | 2/2009 | Metzger et al. |
| 7,695,479 B1 | 4/2010 | Metzger |
| 7,695,520 B2 | 4/2010 | Metzger et al. |
| 7,780,672 B2 | 8/2010 | Metzger et al. |
| 7,789,885 B2 | 9/2010 | Metzger |
| 7,837,690 B2 | 11/2010 | Metzger |
| 7,887,542 B2 | 2/2011 | Metzger et al. |
| 8,123,758 B2 | 2/2012 | Metzger et al. |
| 8,518,047 B2 | 8/2013 | Metzger et al. |
| 8,551,100 B2 | 10/2013 | Metzger |
| 2001/0018589 A1 | 8/2001 | Muller |
| 2001/0034554 A1 | 10/2001 | Pappas |
| 2001/0037155 A1 | 11/2001 | Merchant |
| 2002/0029038 A1 | 3/2002 | Haines |
| 2002/0029045 A1 | 3/2002 | Bonutti |
| 2002/0052606 A1 | 5/2002 | Bonutti |
| 2002/0098304 A1 | 7/2002 | Bailey |
| 2002/0116023 A1 | 8/2002 | Fletcher et al. |
| 2002/0156479 A1 | 10/2002 | Schulzki et al. |
| 2002/0173797 A1 | 11/2002 | Van Zile et al. |
| 2002/0198529 A1 | 12/2002 | Masini |
| 2002/0198531 A1 | 12/2002 | Millard et al. |
| 2003/0028196 A1 | 2/2003 | Bonutti |
| 2003/0040881 A1 | 2/2003 | Steger et al. |
| 2003/0060831 A1 | 3/2003 | Bonutti |
| 2003/0100906 A1 | 5/2003 | Rosa et al. |
| 2003/0100907 A1 | 5/2003 | Rosa et al. |
| 2003/0130665 A1 | 7/2003 | Pinczewski et al. |
| 2003/0171757 A1 | 9/2003 | Coon et al. |
| 2003/0212403 A1 | 11/2003 | Swanson |
| 2003/0216741 A1 | 11/2003 | Sanford et al. |
| 2003/0220641 A1 | 11/2003 | Thelen et al. |
| 2003/0225413 A1 | 12/2003 | Sanford et al. |
| 2004/0039395 A1 | 2/2004 | Coon et al. |
| 2004/0039396 A1* | 2/2004 | Couture et al. ............ 606/87 |
| 2004/0102785 A1 | 5/2004 | Hodorek et al. |
| 2004/0138670 A1 | 7/2004 | Metzger |
| 2004/0220583 A1 | 11/2004 | Pieczynski et al. |
| 2004/0267271 A9 | 12/2004 | Scribner et al. |
| 2005/0027299 A1 | 2/2005 | Metzger |
| 2005/0049603 A1 | 3/2005 | Calton et al. |
| 2005/0113840 A1 | 5/2005 | Metzger et al. |
| 2005/0149038 A1 | 7/2005 | Haines et al. |
| 2005/0149040 A1 | 7/2005 | Haines et al. |
| 2005/0149041 A1 | 7/2005 | McGinley et al. |
| 2005/0149042 A1 | 7/2005 | Metzger |
| 2005/0177170 A1 | 8/2005 | Fisher et al. |
| 2006/0058810 A1 | 3/2006 | Wozencroft et al. |
| 2006/0095049 A1 | 5/2006 | Zannis et al. |
| 2006/0142774 A1 | 6/2006 | Metzger |
| 2006/0142778 A1 | 6/2006 | Dees |
| 2007/0083209 A1 | 4/2007 | Schenberger et al. |
| 2007/0233140 A1 | 10/2007 | Metzger et al. |
| 2007/0282451 A1 | 12/2007 | Metzger et al. |
| 2009/0149859 A1 | 6/2009 | Metzger et al. |
| 2010/0198224 A1 | 8/2010 | Metzger et al. |
| 2010/0318089 A1 | 12/2010 | Metzger et al. |
| 2011/0130762 A1 | 6/2011 | Metzger et al. |
| 2012/0150189 A1 | 6/2012 | Metzger et al. |

FOREIGN PATENT DOCUMENTS

| | | |
|---|---|---|
| DE | 19847701 A1 | 4/2000 |
| DE | 10353345 A1 | 6/2005 |
| EP | 0466659 A3 | 3/1992 |
| EP | 1229414 A2 | 8/2002 |
| EP | 0914806 B1 | 1/2004 |
| EP | 1533770 A1 | 5/2005 |
| EP | 1587425 A2 | 10/2005 |
| EP | 1260183 B1 | 10/2007 |
| FR | 1111677 | 3/1956 |
| JP | 47002838 U | 9/1972 |
| JP | 64029266 | 1/1989 |
| JP | 2501806 | 6/1990 |
| JP | 3504337 | 9/1991 |
| JP | 6233775 A | 8/1994 |
| JP | 0301311 | 4/1995 |
| JP | 7178114 A | 7/1995 |
| JP | 2002501806 A | 1/2002 |
| JP | 2003507117 A | 2/2003 |
| JP | 2009160422 A | 7/2009 |
| JP | 4309397 B2 | 8/2009 |
| WO | WO-8804912 | 7/1988 |
| WO | WO-8804912 A2 | 7/1988 |
| WO | WO-8909028 A1 | 10/1989 |
| WO | WO-9607361 | 3/1996 |
| WO | WO-9729703 | 8/1997 |
| WO | WO-9729703 A1 | 8/1997 |
| WO | WO-9939637 A1 | 8/1999 |
| WO | WO-0113802 A1 | 3/2001 |
| WO | WO-2004064621 A2 | 8/2004 |
| WO | WO-2005046432 A2 | 5/2005 |

OTHER PUBLICATIONS

"AGC Distal Fem Cutter for Dr. Hardy," Biomet, Inc., Jun. 22, 1989.
"AGC Total Knee System, Intramedullary Without Distractor Surgical Technique," 1989, Biomet, Inc.
"AGC Traditional Surgical Overview", copyright 2001 Biomet Orthopedics, Inc.
"AGC-S Total Knee System, Surgical Technique for the AGC-S Total Knee System," 1992, Biomet, Inc.
"Anatomic Axial Alignment Instrumentation," 1994, Biomet, Inc.
"Hand Instruments", High Performance, Precision Series brochure by Arthrotek, copyright 2000.
"NexGen® Complete Knee Solution MIS Quad-Sparing™ Instrumentation," (Mar. 17, 2006) Zimmer, Inc. Web. Jul. 21, 2010. http://www.zimmer.com/ctl?prcat=M3&prod=y&template=MP&action=1&op=global&id . . . 2 pages.

(56) References Cited

OTHER PUBLICATIONS

"pfcSigma.RP-F, High Function Demands Rotation," brochure. (2006) DePuy Orthopaedics, Inc. 2 pages.
"Rotating Platform Knee Technology," tri-fold brochure. (2007) DePuy Orthopaedics, Inc. 2 pages.
"Rotating Platform: Proven," brochure. (2007) DePuy Orthopaedics, Inc. 2 pages.
"Rotating Platform: Unique," brochure. (2007) DePuy Orthopaedics, Inc. 2 pages.
"Sigma High Performance Partial Knee, Unicondylar Surgical Technique," brochure. (2008) DuPuy Orthopaedics, Inc. pp. 1-33.
"Sigma HP Partial Knee," product information sheet. (Feb. 4, 2009).
"Sigma® High Performance Instruments, A high performance knee system demands high performance instruments," advertisement. (2007) DePuy Orthopaedics, Inc. 1 page.
"Sigma® High Performance Instruments, Balanced Surgical Technique," brochure. (2008) DePuy Orthopaedics, Inc. pp. 1-49.
"Sigma® High Performance Instruments, Measured Resection Classic Surgical Technique," brochure. (2008) DePuy Orthopaedics, Inc. pp. 1-48.
"Sigma® High Performance Instruments, Measured Resection Fixed Reference Surgical Technique, Featuring the mini-subvastus approach," brochure. (2007) DePuy Orthopaedics, Inc. pp. 48.
"Sigma® High Performance Instruments, Product Rationale," brochure. (2007) Depuy Orthopaedics, Inc. 12 pages.
"The AGC Revision Knee System Surgical Technique," 1997 Biomet, Inc.
"The Freeman Samuelson Total Knee System," brochure, Biomet, Inc. (1994) 4 pages.
"The Sigma® High Performance Partial Knee: Potential to move more naturally," tri-fold brochure. (2009) DuPuy Orthopaedics, Inc. 2 pages.
"Total Knee Replacement," brochure. (2004) DePuy Orthopaedics, Inc. pp. 1-16.
"What Really Matters," brochure. (2006) DePuy Orthopaedics, Inc. 6 pages.
"Your New Rotating Platform Knee," tri-fold brochure. (2007) DePuy Orthopaedics, Inc. 2 pages.
Genus, brochure entitled "Uni Knee System," Biomet, Inc., Nov. 15, 1998.
Insall/Burstein II Modular Knee System by Zimmer, Inc. copyright 1989.
International Search Report and Written Opinion mailed Jun. 3, 2005 for PCT/US04/00953 claiming benefit of U.S. Appl. No. 10/345,102, filed Jan. 15, 2003.
Keys, Graham W., "Reduced Invasive Approach for Oxford II Medial Unicompartmental Knee Replacement—a Preliminary Study," The Knee, (1999) pp. 193-196.
Microplasty™ minimally invasive knee instruments brochure, Surgical Technique for the Maxim®, Ascent™ and Vanguard™ Total Knee Systems, Biomet Orthopedics, Inc., Feb. 29, 2004.
MIS Minimally Invasive Solution The M/G Unicompartmental Knee Minimally Invasive Surgical Technique, by Zimmer, copyright 2000 (pp. 1-27).
Nex Gen Complete Knee Solution—Intramedually Instrumentation Surgical Technique—For the NexGen Cruciate Retaining & Legacy Posterior Stablized Knee-Publication date unknown, but before Aug. 1, 2001.
NexGen Complete Knee Solution-Extramedullary/Intramedullary Tibial Resector Surgical Technique—Publication date unknown, but before Aug. 1, 2001.
NexGen Complete Knee Solution—Multi-Reference 4-in-1 Femoral Instrumentation—Anterior Reference Surgical Technique—Publication date unknown, but before Aug. 1, 2001.
NexGen Complete Knee Solution—Surgical Technique for the LPS-Flex Fixed Bearing Knee—Publication date unknown, but before Aug. 1, 2001.
Scorpio! Single Axis Total Knee System—Passport Total Knee Instruments—Passport A.R. Surgical Technique by Sryker Howmedica Osteonics, Copyright 2000.
Simple Instruments Surgical Technique for the Knee, copyright 2000 Biomet, Inc.
Surgical Navigation for Total Knee Arthroplasty—Believed to have been presented at the American Academy of Orthopedic Surgeons in Feb. 2001.
The Oxford, brochure entitled "Unicompartmental Knee System", Biomet Orthopedics, Inc., Jul. 15, 2004.
European Search Report for European Patent Application No. 06 013 606.6, dated Nov. 29, 2006; 3 pages.
Translation of the European Search Report dated Nov. 29, 2006 for European Patent Application No. 06 013 060.6; 4 pages.
European Patent Office Action mailed Jun. 6, 2011 for EP Application No. 04702213.2 claiming benefit of PCT/US2004000953, which claims benefit of U.S. Appl. No. 10/345,102, filed Jan. 15, 2003.
European Patent Office Action mailed May 21, 2012 for EP Application No. 04702213.2 claiming benefit of PCT/US2004000953, which claims benefit of U.S. Appl. No. 10/345,102, filed Jan. 15, 2003.
European Patent Office Action mailed Sep. 21, 2010 for EP Application No. 04702213.2 claiming benefit of PCT/US2004000953, which claims benefit of U.S. Appl. No. 10/345,102, filed Jan. 15, 2003.
European Patent Office Supplementary Search Report mailed Apr. 23, 2010 for PCT/US2004000953, claiming benefit of U.S. Appl. No. 10/345,102, filed Jan. 15, 2003.
Insall/Burstein II Modular Knee System by Zimmer, Inc. 20 pages, 1989.
Japanese Office Action mailed Aug. 2, 2011 for JP Application No. 2009-057755 filed Mar. 11, 2009, claiming benefit of JP Serial No. 2005-518807 filed Jan. 14, 2004; which claims benefit of PCT/US2004/000953 filed Jan. 14, 2004; which claims benefit of U.S. Appl. No. 10/345,102, filed Jan. 15, 2003.
Japanese Office Action mailed Nov. 11, 2008 for JP Application No. 2005-518807 filed Jul. 15, 2005, which claims benefit of PCT/US2004/000953 filed Jan. 14, 2004; which claims benefit of U.S. Appl. No. 10/345,102, filed Jan. 15, 2003.
McGinty, M.D., Operative Arthroscopy, Department of Orthopaedic Surgery, Medical University of South Carolina, Charleston, South Carolina, copyright 1991 by Raven Press, Ltd., (2 pages).
Nex Gen Complete Knee Solution—Intramedually Instrumentation Surgical Technique—For the NexGen Cruciate Retaining & Legacy Posterior Stablized Knee-Publication 1994.
NexGen Complete Knee Solution—Extramedullary/Intramedullary Tibial Resector Surgical Technique—2008.
NexGen Complete Knee Solution—Surgical Technique for the LPS-Flex Fixed Bearing Knee, 2000.

\* cited by examiner

FEMORAL GUIDE FOR IMPLANTING A FEMORAL KNEE PROSTHESIS

CROSS-REFERENCE TO RELATED APPLICATIONS

This application is a continuation of U.S. patent application Ser. No. 12/367,903 filed on Feb. 9, 2009, which is a continuation of U.S. patent application Ser. No. 10/730,456 filed on Dec. 8, 2003, issued on Feb. 10, 2009 as U.S. Pat. No. 7,488,324. The entire disclosure of the above application is incorporated herein by reference.

FIELD

The present disclosure relates generally to the alignment hardware used in a surgical procedure and, more particularly, to an alignment hardware used in the implantation of a femoral prosthesis.

BACKGROUND

The implantation of knee prosthetics require the distal end of the femur to be prepared to receive a femoral component of the knee prosthetic. This preparation generally requires the resection of various surfaces of the femur to ensure the proper coupling of the knee prosthetic to the resected surfaces. Various guides are known to assist the surgeon in locating cutting blades used to resect the femur.

The location and size of cuts to the femur generally correspond to internal surfaces within the femoral prosthetics. The location of the surfaces may change depending on the size of the prosthetics used. To this end, a femoral sizing guide is used to determine the size of the femoral prosthetic which will be implanted at the implantation site of the particular patient.

Femoral knee prosthesis are made available in a range of standard sizes. A femoral sizing guide is used to assist the selection of a standard sized femoral knee prosthetic which will best fit the requirements of a particular implantation site. The size and orientation of the implant is a function of kinematic and biomechanical considerations. In this regard, the femoral sizing guide is used to measure the condyles of the patient's femur and specifies the proper location of guiding apertures within the femur. As such, it is necessary to provide a reliable femoral sizing guide which is configured to allow the surgeon to determine the size and proper orientation of the femoral implant.

SUMMARY

Disclosed is a method of selecting a femoral prosthetic for implantation relative to a femur using a femoral sizing guide. An extension portion of the femoral sizing guide can be placed adjacent to a posterior condyle surface of the femur. A stylus can be located proximate to an interior condyle surface of the femur. A first actuator disposed between the extension portion and a base portion can be moved to rotatably displace the extension portion with respect to the base portion until the stylus is centrally located on top of the interior condyle. A measurement of the femur can be identified with the sizing guide based on a relative location of the stylus, the extension portion and the base portion. A femoral prosthesis can be selected based on the measurement.

According to additional features, the stylus can be translated along an axis relative to the base portion. A superstructure associated with the stylus can be translated along the axis relative to the extension portion. Translating the stylus can include rotating a second actuator causing a threaded distal end of the second actuator to rotate within a threaded hole of the base portion. Moving the first actuator can include rotating a worm gear disposed between the extension portion and the base portion. Identifying the measurement can include identifying a first gradation of a plurality of indexing gradations provided on a worm gear mount of the worm gear. Identifying the measurement can further include identifying a second gradation of a series of gradations provided on the stylus. At least one retaining hole can be drilled into the femur while referencing drilling guides extending from the base portion.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The present disclosure will become more fully understood from the detailed description and the accompanying drawings, wherein:

FIG. 6 is a side view of the femoral sizing guide coupled to a resected femur;

DETAILED DESCRIPTION

The following description is merely exemplary in nature and is in no way intended to limit the disclosure, its application, or uses.

Figure 1:
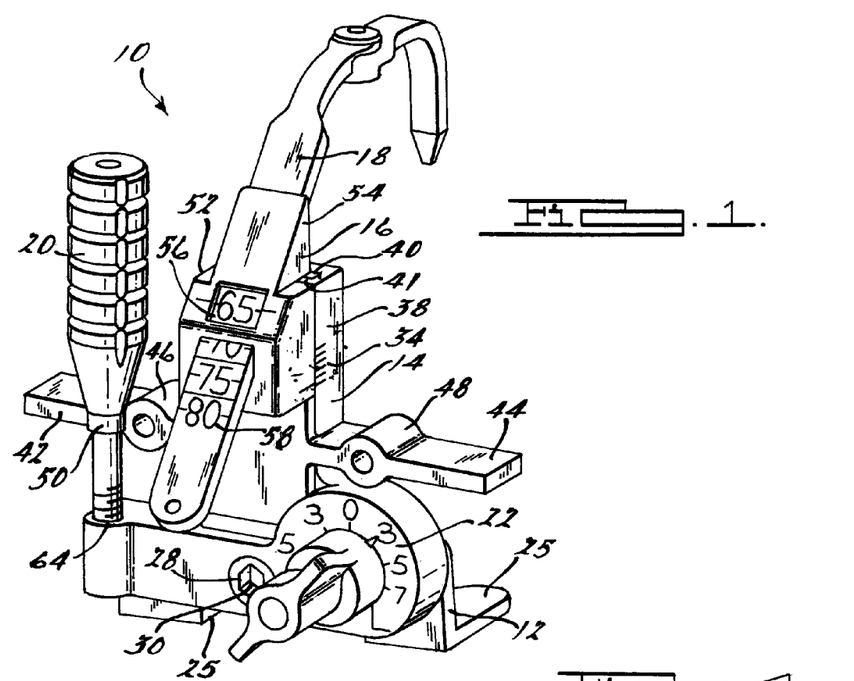
FIG. 1 represents a perspective view of the femoral sizing guide of the present disclosure.
Figure 2:
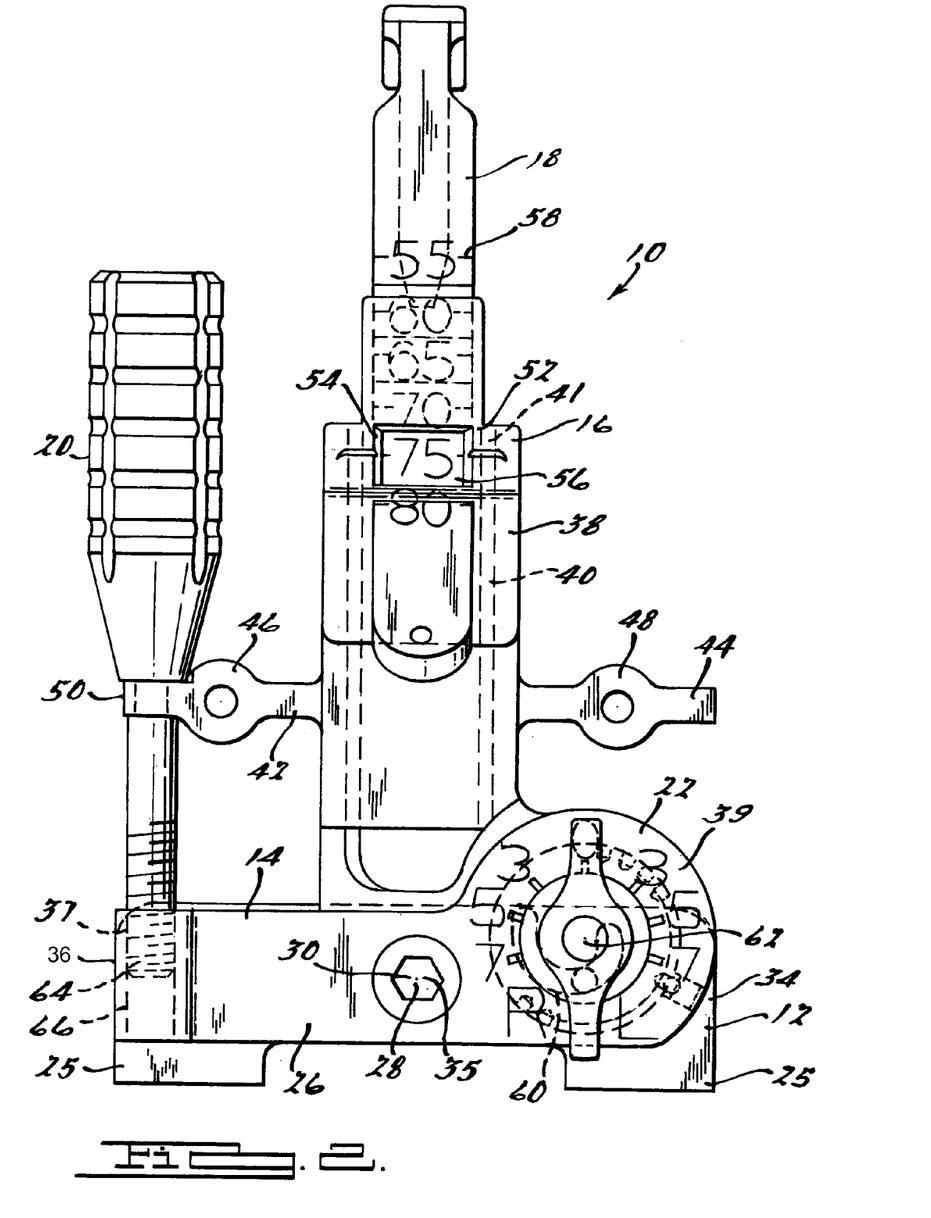
FIG. 2 represents a front view of the femoral sizing guide shown in FIG. 1.

Referring generally to FIGS. 1 and 2, a femoral sizing guide 10 according to the teachings of the present disclosure is shown. The femoral sizing guide 10 is generally formed of an extension portion 12, a base portion 14, a superstructure portion 16 having a corresponding graduated stylus 18, an actuator 20 disposed between the superstructure 16 and the base portion 14, and a worm gear 22. The femoral sizing guide 10 is configured to measure the size and general angular orientation of the condyles of a femur to allow a treating physician to interoperatively select a proper femoral prosthetic.

The feet 25 of the extension portion 12 use the posterior sides of the condylar surfaces as a reference. As the surfaces of the condyles can be degraded due to natural causes, their ability to function as a reference surface and, therefore, indexing plane can be degraded. As such, adjustability of the feet 25 can assist in the alignment of the sizing guide.

Figure 3:
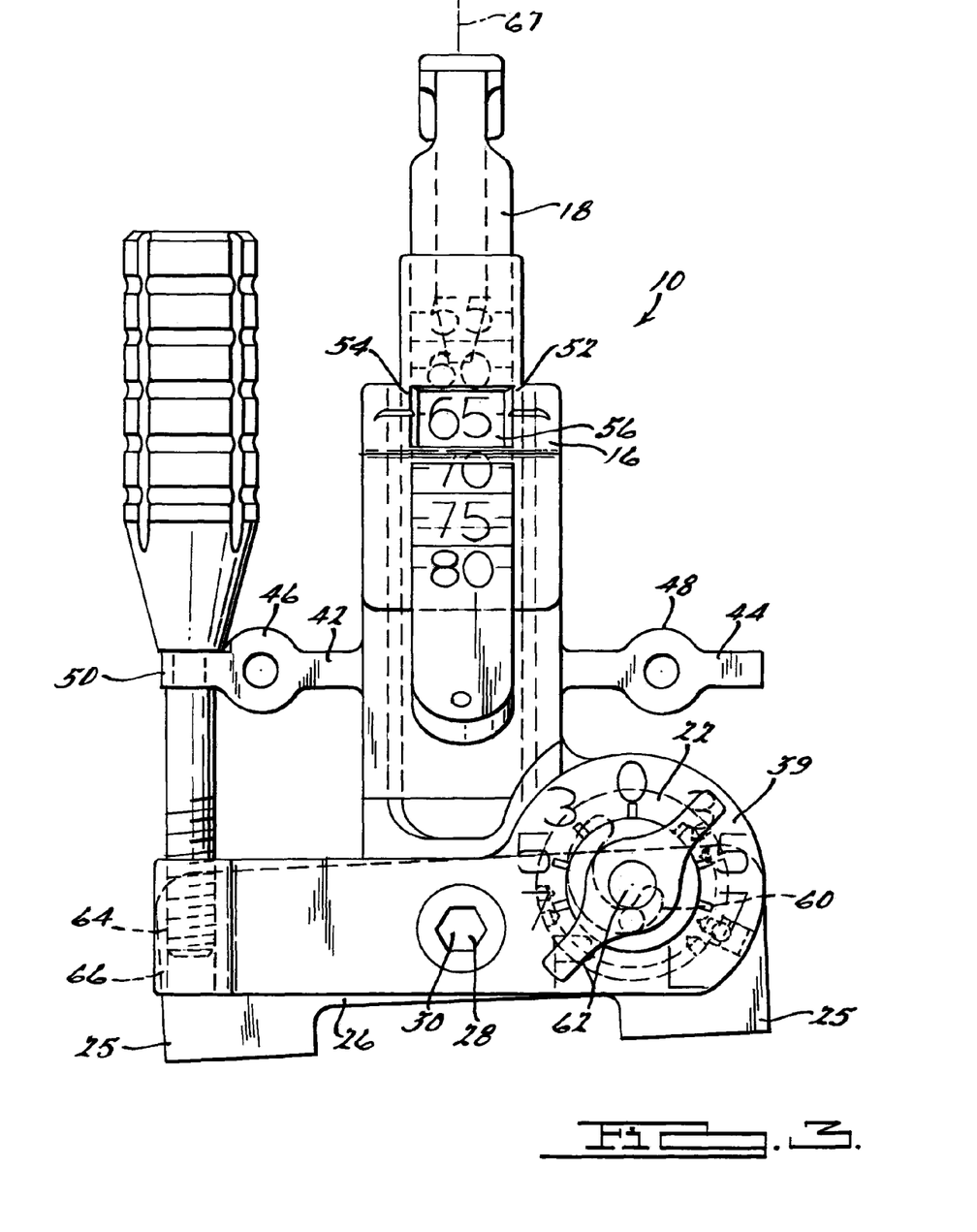
FIG. 3 represents a femoral sizing guide shown in FIG. 1 with the worm gear actuated.

As best seen in FIGS. 2 and 3, the extension portion has a pair of feet 25 coupled to a central member 26. The extension portion 12 is pivotally coupled to the base portion 14 at a central pivot point 28 through a pivot axis 30. Further disposed between the extension portion 12 and the base portion 14 is a worm gear 22 which functions to rotate the extension portion 12 and corresponding feet 25 about the pivot axis 30 in a predetermined and repeatable fashion. The extension portion 12 further has a depending pin or flange 32 which defines a first portion of the worm gear 22.

The base portion 14 has a body 34 having a body pivot point 35 which corresponds to the pivot axis 30. A body 34 defines a support flange 38 having a support flange track 40 which is configured to interface with a superstructure track 41. Defined on a first side 36 of the body 34 is a threaded coupling portion 37. The threaded coupling portion 37 is configured to be coupled to the actuator 20. A second side 45 of the body 34 defines a worm gear mount 39. The worm gear mount 39 defines an aperture 43 and further has a plurality of indexing gradations which will be used by a treating physician to determine the amount of rotation of the feet 25 with respect to the base portion 14 about pivot axis 30. It should be noted that the pivot axis 30 is offset a predetermined distance from the transepicondylar axis of the femur.

The superstructure 16 has a pair of depending side flanges 42 and 44 which define drilling guides 46 and 48. The first depending side flange 42 further defines a coupling mechanism 50 which is shown in the form of an aperture to rotatably support and guide the second actuator 20. The superstructure 16 further has a holding mechanism 52 which defines an indexed slot 54 which slidably receives the graduated stylus 18. The holding mechanism 52 further defines a window 56 which displays graduations 58 of the graduated stylus 18.

As best seen in FIG. 3, the extension portion 12 can be rotated about the pivot axis 30 by the rotation of the first actuator or worm gear 22. In this regard, the worm gear 22 defines an arcuate slot 60 which is rotatable about a gear pivot point 62. The arcuate slot 60 slidably holds the fixed worm gear pin 32. The rotation of the arcuate slot 60 about the coupling point 62 causes the rotation of the extension portion 12 with respect to the base portion 14. Similarly, it causes rotation with respect to the superstructure 16 and the stylus 18. The worm gear has a system of associated graduations which allow a treating physician to categorize the necessary rotation of the measurement guide about the central pivot axis 30.

The actuator 20 functions to translate the superstructure portion 16 with respect to the extension portion 12 or the base portion 14. In this regard, the rotation of the actuator 20 causes a threaded distal end 64 of the actuator 20 to rotate within a threaded hole 66 in the coupling portion 37 of the base portion 14. This causes the superstructure portion 16 and stylus 18 to translate in a second axis 67 away from or toward the base portion 14 and associated feet 25 of the extension portion 12. The movement causes translation of the drill guides 46 and 48 with respect to the feet 25 and the resected femur.

Figure 4:
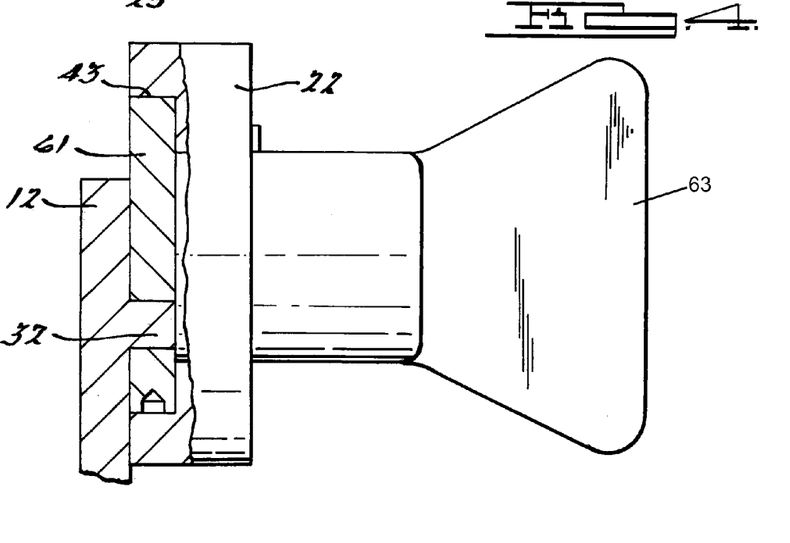
FIG. 4 is a cross-sectional view of the worm gear mechanism shown in FIG. 2.

FIG. 4 represents a cross-sectional view of the worm gear 22. As seen, the extension portion 12 has a depending pin 32 which interfaces with the arcuate slot 60 defined in a first rotating member 61. The rotating member 61 and associated handle portion 63 are rotatably coupled to the worm gear mount 39 of the base portion 14. The worm gear mount 39 has a plurality of gradations which indicate the relative rotations of the extension portion 12 with respect to the base portion 14 and associated superstructure 16.

Figure 5:
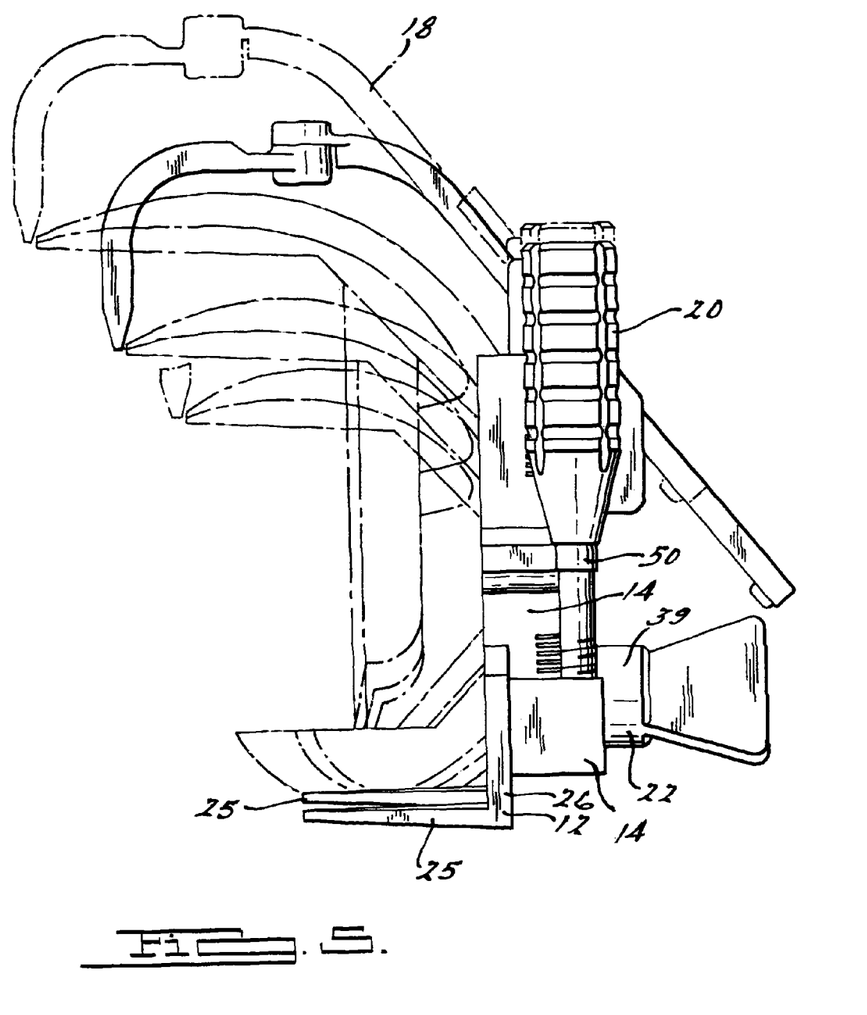
FIG. 5 represents a side view of the femoral sizing guide measuring a plurality of insert sizes.

Shown in FIGS. 5 and 6, the graduated stylus 18 rests against the anterior cortex of the femur at an anterior/posterior location. Angular adjustment of the extension portion 12 with respect to the base portion 14 is made by rotating the worm gear 22 and adjusting the actuator 20 so as to allow for the proper standard size femoral implant to be used. In this regard, the adjustments allow the surgeon to properly position the drilling guides 46 and 48 so as to allow a proper positioning of the guide holes (not shown). The holes drilled using the drilling guides 46 and 48 are used to position a cutting guide (not shown) which is used to make cuts to form surfaces which correspond to internal planar surfaces on the interior surface of the femoral prosthetic 80.

As shown in FIGS. 3, 5, and 6, the feet 25 of the extension portion 12 are positioned adjacent to the posterior side of the femoral condyles. The location of the tip of the stylus 18 is adjusted by sliding the stylus 18 within the index slot 54 of the holding mechanism 52. Further adjustment can be made by adjusting the position of the superstructure 16 with respect to the extension portion by rotating the actuator 20.

At this point, the worm gear 22 is rotated so as to centrally locate the tip of the stylus 18 on top of the interior condyle surface. The treating physician reads values from the graduated stylus 18, actuator 20, and indexed worm gear 22 to select the appropriate femoral prosthetic. A pair of retaining holes are then bore into the resected femur using the drilling guides 46 and 48.

FIGS. 7-12 represent a second embodiment of the present disclosure. Shown is a modular system which allows a treating physician to interoperatively assemble the femoral sizing guide 10*b*. This allows the treating physician to use a rotatable foot portion 25*a* or a non-rotatable foot portion 25*b*. Additionally, the treating physician can utilize varying types of superstructure 16*a* or 16*b*.

Figure 7:
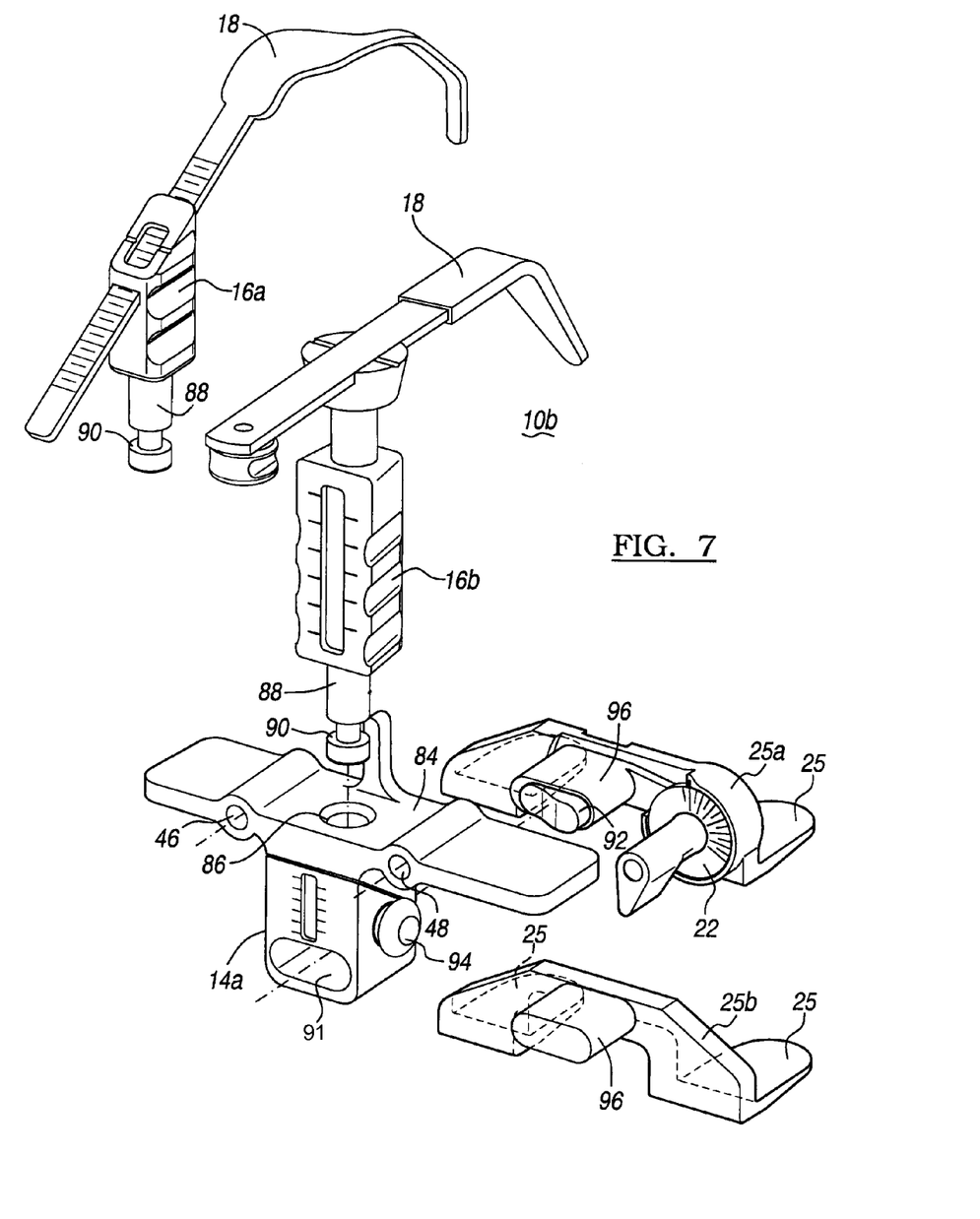
FIGS. 7 and 8 are exploded views of a femoral measurement guide according to another embodiment of the present disclosure.
Figure 8:
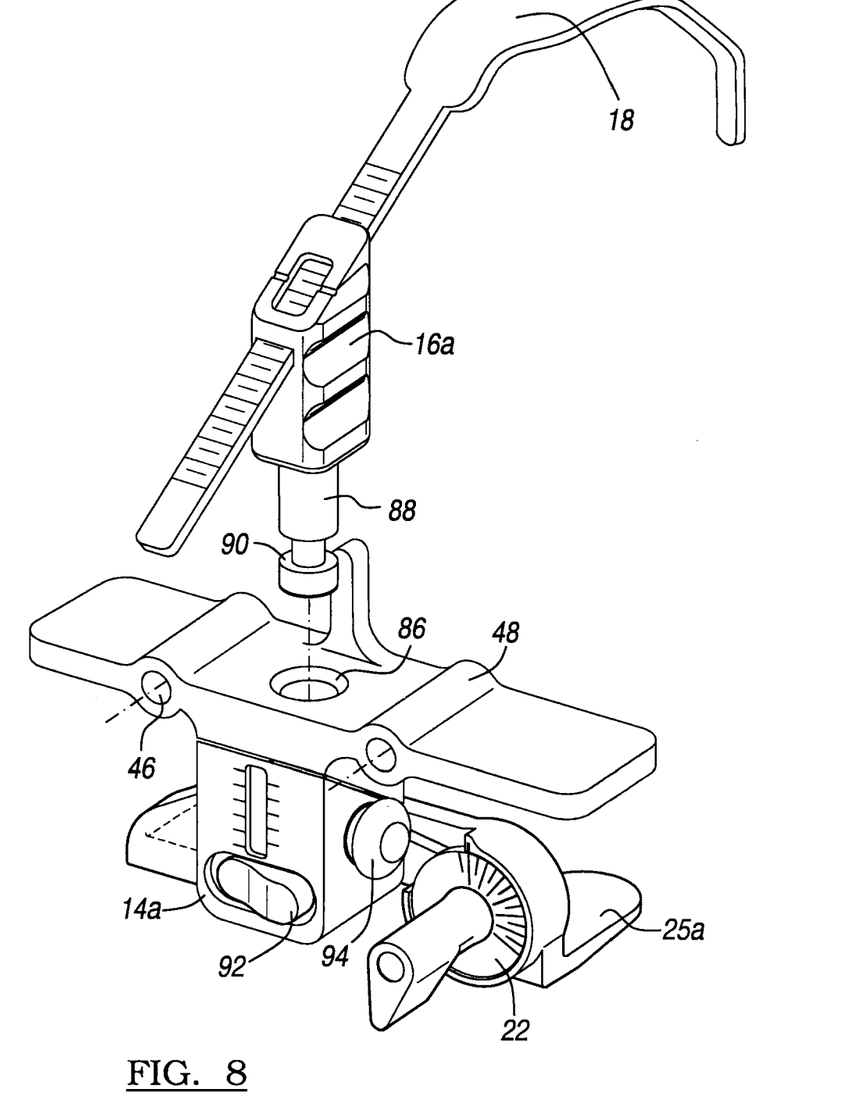

FIGS. 7 and 8 represent an exploded view of the femoral sizing guide 10*b* according to the teachings of a second embodiment of the disclosure. Shown is a base portion 14*a* which defines a coupling mechanism for coupling either the first or second superstructure 16*a* or 16*b* to the top surface 84 of the base portion 14*a*. As shown, the coupling mechanism can take the form of an aperture 86 defined in the top surface 84 which is configured to fixably receive a post 88 formed on the superstructure 16*a* or 16*b*. The post 88 can optionally have a locking feature 90 which allows the post to be non-rotatably and yet releasably coupled to the base 14*a*.

Additionally, the base 14*a* defines a second coupling mechanism 91 which is configured to couple the base 14*a* to either one of the rotatable foot portion 25*a* or the non-rotatable foot portion 25*b*. The coupling mechanism 91 is shown as an elliptical bore defined in the base 14*a*. The elliptical bore 91 corresponds to an elliptical coupling structure defined on the foot portions 25*a* or 25*b*.

Components which are coupled to base portion 14*a* can be removed by releasing a spring loaded locking mechanism 92 defined on the elliptical structure on the foot portion 25*a*. It is envisioned the spring loaded locking mechanism 92 can be positioned on the base 14*a*.

Figure 10:
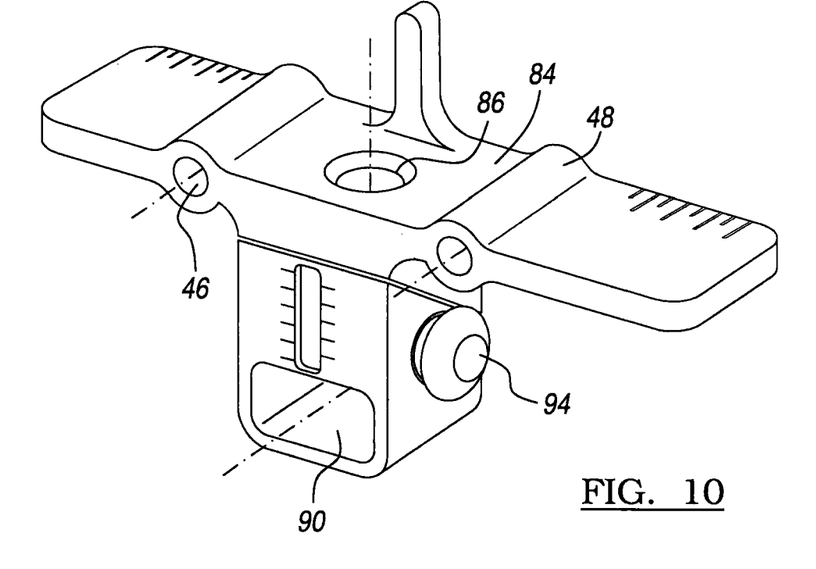
FIG. 10 is a base portion shown in FIG. 7.

As shown in FIGS. 7, 8, and 10, the base 14*a* is configured to allow translation of the drilling guides 46 and 48 with respect to the foot portion 25*a*. Shown is a knob 94, which is coupled to an internal gear (not shown) which causes the relative translation. It is envisioned that the actuator shown in FIG. 1 can additionally be used to adjust the relative location of the superstructure portion 16 with respect to the foot portion 25*a*.

Figure 9:
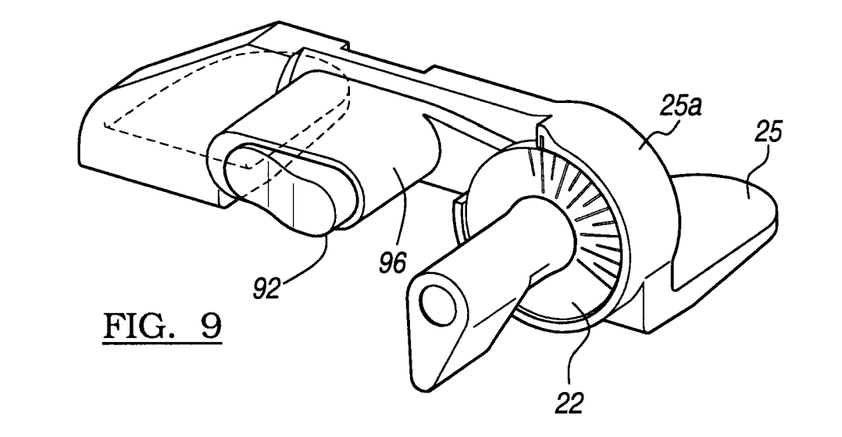
FIG. 9 is a modular adjustable foot portion shown in FIG. 7.

As best seen in FIG. 9, the adjustable foot portion 25a has a rotational mechanism which allows for rotation of the feet 25 with respect to the coupling mechanism 91. In this regard, the adjustable foot portion 25a has an oval post 96, about which the feet 25 are rotatably coupled. As described above with respect to the first embodiment, rotation of the worm gear 22 causes rotation of the feet with respect to the base portion 14a.

Figures 11, 12:
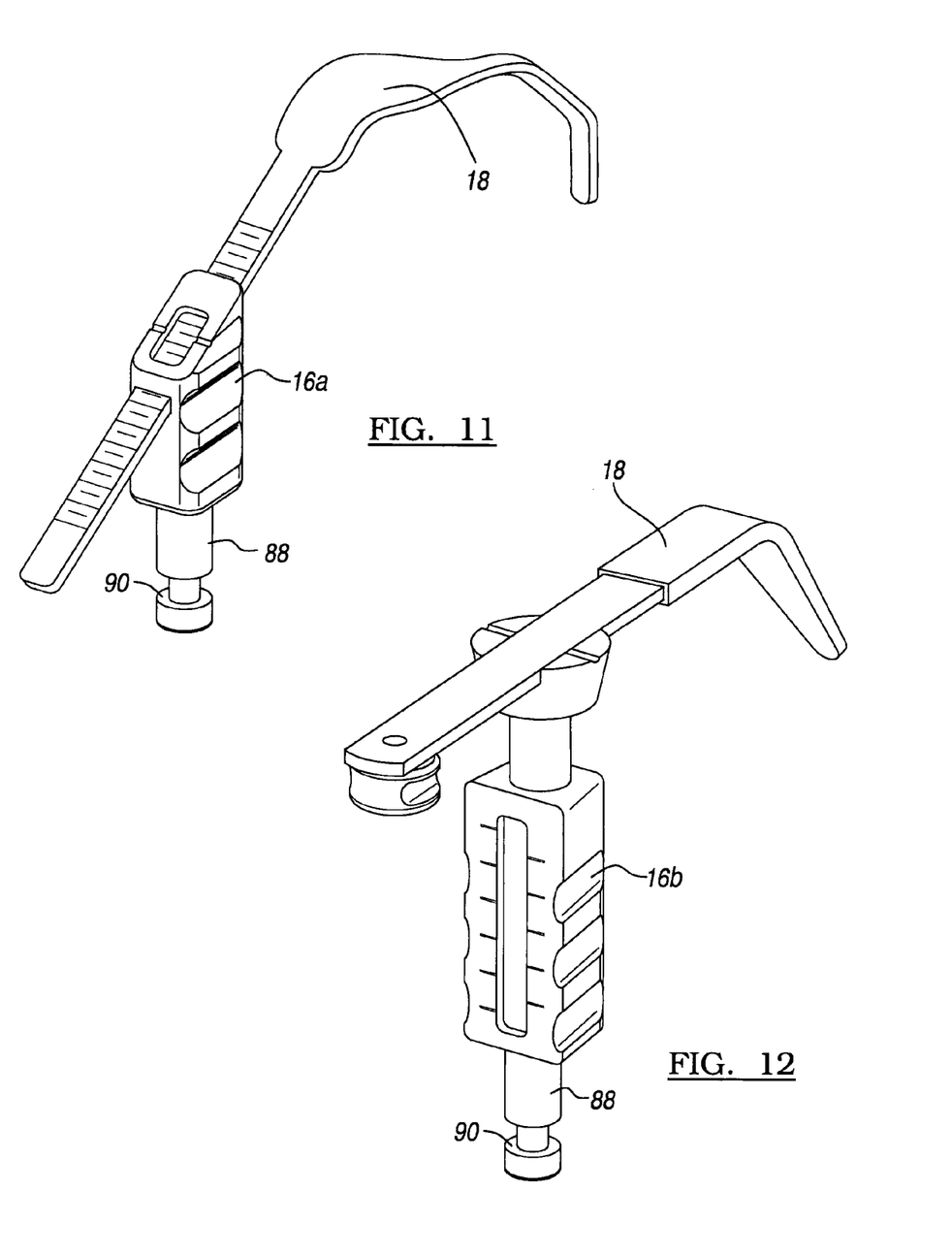
FIGS. 11 and 12 are modular superstructures shown in FIG. 7.

FIGS. 11 and 12 represent modular superstructure 16a and 16b. The superstructures are configured to be adjusted in a fashion which allows the treating physician to measure anatomical features of a resected bone. The location of the tip of the stylus 18 can be measured by vertical and horizontal adjustment of the superstructure 16b or by angular movement shown in superstructure 16a.

The description of the disclosure is merely exemplary in nature and, thus, variations that do not depart from the gist of the disclosure are intended to be within the scope of the disclosure. Such variations are not to be regarded as a departure from the spirit and scope of the disclosure.

What is claimed is:

1. A method of selecting a femoral prosthetic for implantation relative to a femur using a femoral sizing guide, the method comprising:
    placing an extension portion of the femoral sizing guide adjacent to a posterior condyle surface of the femur, the extension portion having a base portion pivotally connected thereto;
    locating a stylus proximate to an interior condyle surface of the femur;
    moving a first actuator disposed between the extension portion and the base portion to rotatably displace the extension portion with respect to the base portion until the stylus is centrally located on top of the interior condyle;
    identifying a measurement of the femur with the sizing guide based on a relative location of the stylus, the extension portion and the base portion; and
    selecting a femoral prosthesis based on the measurement;
    wherein moving the first actuator comprises rotating a worm gear disposed between the extension portion and the base portion.

2. The method of claim 1, further comprising: translating the stylus along an axis relative to the base portion.

3. The method of claim 2 wherein translating the stylus further comprises translating a superstructure associated with the stylus along the axis and relative to the extension portion.

4. The method of claim 3 wherein translating the stylus comprises rotating a second actuator causing a threaded distal end of the second actuator to rotate within a threaded hole of the base portion.

5. The method of claim 2 wherein translating the stylus comprises translating the stylus relative to drill guides extending from the superstructure.

6. The method of claim 1 wherein identifying the measurement comprises identifying a first gradation of a plurality of indexing gradations provided on a worm gear mount of the worm gear.

7. The method of claim 6 wherein identifying the measurement further comprises identifying a second gradation of a series of gradations provided on the stylus.

8. The method of claim 1, further comprising:
    drilling at least one retaining hole into the femur referencing drilling guides extending from the superstructure.

9. A method of selecting a femoral prosthetic for implantation relative to a femur using a femoral sizing guide, the method comprising:
    placing an extension portion of the femoral sizing guide adjacent to a posterior condyle surface of the femur, the extension portion having a base portion pivotally connected thereto;
    locating a stylus extending from a superstructure proximate to an interior condyle surface of the femur;
    sliding the stylus within an index slot of the superstructure to position a tip of the stylus relative to the interior condyle surface of the femur;
    rotatably displacing the extension portion with respect to the base portion until the stylus is centrally located on top of the interior condyle by moving a first actuator;
    translating a superstructure associated with the stylus along an axis and relative to the extension portion by rotating a second actuator, the second actuator is laterally spaced apart from the axis;
    identifying a measurement of the femur with the sizing guide based on a relative location of the stylus, the extension portion and the base portion; and
    selecting a femoral prosthesis based on the measurement.

10. The method of claim 9 wherein rotatably displacing the extension portion comprises moving a first actuator disposed between the extension portion and the base portion.

11. The method of claim 10 wherein translating the superstructure comprises rotating the second actuator causing a threaded distal end of the second actuator to rotate within a threaded hole of the base portion.

12. The method of claim 10 wherein translating the superstructure moves drill guides relative to the base portion.

13. The method of claim 10 wherein rotatably displacing the extension portion comprises rotating a worm gear disposed between the extension portion and the base portion.

14. The method of claim 13 wherein identifying the measurement comprises identifying a first gradation of a plurality of indexing gradations provided on a worm gear mount of the worm gear.

15. The method of claim 14 wherein identifying the measurement further comprises identifying a second gradation of a series of gradations provided on the stylus.

16. The method of claim 8, further comprising:
    drilling at least one retaining hole into the femur referencing drilling guides extending from the superstructure.

17. A method of selecting a femoral prosthetic for implantation relative to a femur using a femoral sizing guide, the method comprising:
    placing an extension portion of the femoral sizing guide adjacent to a posterior condyle surface of the femur, the extension portion having a base portion pivotally connected thereto;
    locating a stylus extending from a superstructure proximate to an interior condyle surface of the femur;
    sliding the stylus within an index slot of the superstructure to position a tip of the stylus relative to the interior condyle surface of the femur;
    rotating a worm gear disposed between the extension portion and the base portion to displace the extension portion with respect to the base portion until the stylus is centrally located on top of the interior condyle;
    translating the stylus relative to the base portion;
    identifying a measurement of the femur with the sizing guide based on a relative location of the stylus, the extension portion and the base portion; and
    selecting a femoral prosthesis based on the measurement.

18. The method of claim 17 wherein translating the stylus comprises rotating an actuator causing a threaded distal end of the actuator to rotate within a threaded hole of the base portion.

* * * * *